US011351287B2

(12) United States Patent
Zihlmann et al.

(10) Patent No.: US 11,351,287 B2
(45) Date of Patent: *Jun. 7, 2022

(54) BONE SUBSTITUTE MATERIAL

(71) Applicant: GEISTLICH PHARMA AG, Wolhusen (CH)

(72) Inventors: Claudio Zihlmann, Lucerne (CH); Michael Bufler, Reinach (CH)

(73) Assignee: Geistlich Pharma AG, Wolhusen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/220,331

(22) Filed: Dec. 14, 2018

(65) Prior Publication Data

US 2019/0184059 A1 Jun. 20, 2019

(30) Foreign Application Priority Data

Dec. 14, 2017 (EP) .................................... 17207235

(51) Int. Cl.
| | | |
|---|---|---|
| *A61L 27/12* | (2006.01) | |
| *A61L 27/58* | (2006.01) | |
| *A61L 27/46* | (2006.01) | |
| *A61L 27/50* | (2006.01) | |
| *A61L 24/00* | (2006.01) | |
| *A61L 27/42* | (2006.01) | |
| *A61L 27/56* | (2006.01) | |
| *B33Y 80/00* | (2015.01) | |
| *A61L 27/32* | (2006.01) | |

(52) U.S. Cl.
CPC ........... *A61L 27/12* (2013.01); *A61L 24/0063* (2013.01); *A61L 27/425* (2013.01); *A61L 27/46* (2013.01); *A61L 27/56* (2013.01); *A61L 27/58* (2013.01); *A61L 27/32* (2013.01); *A61L 2400/12* (2013.01); *A61L 2400/18* (2013.01); *A61L 2430/02* (2013.01); *B33Y 80/00* (2014.12)

(58) Field of Classification Search
CPC ...... A61L 2430/02; A61L 27/46; A61L 27/12; A61L 27/32; A61L 27/56; A61L 27/58; A61L 27/425; A61L 2400/18; A61L 27/273608; A61L 27/50; A61L 27/365; A61F 2/28; A61F 2002/2835; A61F 2002/3093; A61F 2310/00293; A61K 33/42; A61K 35/19

See application file for complete search history.

(56) References Cited

U.S. PATENT DOCUMENTS

| | | | |
|---|---|---|---|
| 5,167,961 A | 12/1992 | Heinz | |
| 5,352,715 A | 10/1994 | Wallace et al. | |
| 5,958,504 A | 9/1999 | Lee | |
| 7,322,825 B2 | 1/2008 | Szymaitis | |
| 8,734,524 B2 | 5/2014 | Bufler | |
| 9,066,995 B2 | 6/2015 | Bufler | |
| 2003/0026770 A1 | 2/2003 | Szymaitis | |
| 2007/0026030 A1 | 2/2007 | Gill | |
| 2012/0107401 A1 | 5/2012 | McKay | |
| 2012/0130506 A1 | 5/2012 | Bufler | |
| 2014/0127392 A1 | 5/2014 | Berckmans, III | |
| 2015/0024023 A1 | 1/2015 | Gibson | |
| 2016/0106674 A1 | 4/2016 | Scalesciani | |
| 2016/0144071 A1 | 5/2016 | Bufler | |
| 2019/0209735 A1 | 7/2019 | Suppiger et al. | |
| 2019/0209737 A1 | 7/2019 | Zihlmann et al. | |
| 2020/0016293 A1 | 1/2020 | Zihlmann et al. | |

FOREIGN PATENT DOCUMENTS

| | | | | |
|---|---|---|---|---|
| DE | 102011050183 A1 | * | 11/2012 | ......... A61F 2/30771 |
| EP | 0 270 254 A2 | | 6/1988 | |
| EP | 2654816 B1 | | 2/2015 | |
| WO | 2010/149296 A1 | | 12/2010 | |

OTHER PUBLICATIONS

Geistlich Bio-Oss et al: "Proven Clinical Efficiency Key to Success of Nascent European Bone Graft Substitutes Market", PR Newswire, Sep. 6, 2004 (Sep. 6, 2004), XP55566242, Retrieved from the Internet: URL:https://www.geistlich-na.com/fileadmin/contenVGeistlich_USA/Documents/PDFs/Product_Brochures/GPNA-BoneSubstituteBrochure_2018.pdf.

Daniele Cardaropoli et al: "Bio-Oss collagen and orthodontic movement for the treatment of infrabony defects in the esthetic zone", The International journal of periodontics & restorative dentistry, Dec. 1, 2006 (Dec. 1, 2006), p. 553, XP55566245, United States Retrieved from the Internet: URL:http://coimplante.odo.br/Biblioteca/J%20Peridontics%20Restorative%20DenVprd_26_6_Cardaropoli_4.pdf.

Adileh Shirmohammadi et al., "Comparative Study on the Efficacy of Anorganic Bovine Bone (Bio-Oss) and Nanocrystalline Hydroxyapatite (Ostim) in Maxillary Sinus Floor Augmentation", International Scholarly Research Notices, vol. 2014, Jan. 1, 2014 (Jan. 1, 2014), pp. 1-7, XP55566246, DOI: 10.1155/2014/967091.

Notification of Transmittal of The International Search Report and the Written Opinion of the International Searching Authority, or the Declaration dated Mar. 19, 2019 cited in PCT/EP2018/085018, 13 pages.

(Continued)

*Primary Examiner* — Tracy Liu

(74) *Attorney, Agent, or Firm* — Rothwell, Figg, Ernst & Manbeck, P.C.

(57) ABSTRACT

A biphasic calcium phosphate/hydroxyapatite (CAP/HAP) bone substitute material having a sintered CAP core and a closed epitactically grown layer of nanocrystalline HAP deposited on the external surface of the sintered CAP core, wherein the closed epitactically grown layer of nanocrystalline HAP deposited on the external surface of the sintered CAP core has a homogeneous coarse external surface comprising flat crystal platelets, which shows an enhanced osteogenic response, a method of promoting bone formation, bone regeneration and/or bone repair by implanting the biphasic calcium phosphate/hydroxyapatite (CAP/HAP) bone substitute material, and a process of preparation thereof.

20 Claims, 6 Drawing Sheets

(56) References Cited

OTHER PUBLICATIONS

Extended European Search Report cited in European Application No. 17207341.3, dated Jun. 6, 2018, 10 pages.
Written Opinion of the International Searching Authority in PCT/EP2018/084783, dated Jun. 20, 2019, 6 pages.
Sheikh et al. "Natural graft tissues and synthetic biomaterials for periodontal and alveolar bone reconstructive applications: a review," Biomaterials Research, published Jun. 5, 2017, p. 1-20.
Gittens et al. Implant Osseointegration and the Role of Microroughness and Nanostructures: Lessons for Spine Implants. Acta Biomater. Author manuscript. Aug. 1, 2015. (Year: 2015).
Intention to Grant cited in European Application No. 18 816 062.6 dated Feb. 6, 2020, 6 pages.
Borum-Nicholas, L., et al: "Surface modification of hydroxyapatite. Part I. Dodecyl alcohol", Biomateri, Elsevier Science Publishers BV., Barking, GB, vol. 24, No. 21, 1(2003), pp. 3671-3679.
European Search Report cited in EP 17207235, dated Jun. 12, 2018, 6 pages.
Dikova, et al., "Dimensions Accuracy in Different Laser Cutting Schemes"; Scientific Proceedings VIII International Congress "Machines, Technologies, Materials", Year XIX, vol. 1, pp. 30-33 (2011).
Sun et al., "Direct selective laser melting of Hydroxyapatite without using binder", Osaka University, Division of Materials & Manufacturing Science, Japan, Frontiers, Mar. 30, 2016. https://www.frontiersin.org/10.3389/conf.FBIOE.2016.01.02366/event_abstract.
Ansari, et al. "Investigation of SLM Process in Terms of Temperature Distribution and Melting Pool Size: Modeling and Experimental Approaches"; Materials; Apr. 2019, pp. 1-18 doi:10.3390/ma12081272.
Liao, et al. "Thermal decomposition and reconstitution of hydroxyapatite in air atmosphere," Biomaterials, 20 (1999) 1807-1813.

* cited by examiner

* surface coverage by individual clusters of flat crystal platelets as measured by SEM

BONE SUBSTITUTE MATERIAL

CROSS-REFERENCE TO RELATED APPLICATIONS

The present application claims priority benefit of European Patent Application No. 17207235.7, filed on Dec. 14, 2017, the disclosure of which is incorporated herein by reference.

BACKGROUND

The invention relates to a new biphasic bone substitute material with a bilayer structure based on calcium phosphate/hydroxyapatite (CAP/HAP) which has a homogeneous coarse external surface, a process for preparing that material and the use thereof as implant or prosthesis to support bone formation, bone regeneration, bone repair and/or bone replacement at a defect site in a human or animal.

Defects in bone structure arise in a variety of circumstances, such as trauma, disease, and surgery and there is still a need for effective repair of bone defects in various surgical fields.

Numerous natural and synthetic materials and compositions have been used to stimulate healing at the site of a bone defect. A well known natural, osteoconductive bone substitute material that promotes bone growth in periodontal and maxillofacial osseous defects is Geistlich Bio-Oss®, commercially available from Geistlich Pharma AG. That material is manufactured from natural bone by a process described in U.S. Pat. No. 5,167,961, which enables preservation of the trabecular architecture and nanocrystalline structure of the natural bone, resulting in an excellent osteoconductive matrix which is not or very slowly resorbed.

Tricalcium phosphate/hydroxyapatite (TCP/HAP) systems and their use as bone substitute materials are described, for example, in U.S. Pat. No. 6,338,752 disclosing a process for preparing a biphasic cement of α-TCP/HAP by heating a powder mixture of ammonium phosphate and HAP at 1200-1500° C.

European Patent EP-285826 describes a process for the production of a layer of HAP on metallic and non-metallic bodies for implants by application of a layer of α-TCP and completely converting the α-TCP layer into HAP by reaction with water of pH 2 to 7 at 80-100° C. The product obtained is a metallic or non metallic body covered with a layer of HAP.

WO 97/41273 describes a process for coating a substrate such as notably hydroxyapatite (HAP) or other calcium phosphates (CAP) with a coating of carbonated hydroxyapatite, i.e. hydroxyapatite wherein phosphate and/or hydroxyl ions are partially replaced by bicarbonate ions, by a process comprising (a) immersing the substrate in a solution of pH 6.8 to 8.0 containing calcium ions, phosphate ions and bicarbonate ions at a temperature lower than 50° C., (b) heating the portion of the solution in contact with the substrate to a temperature of 50 to 80° C. until having a pH greater than 8, (c) maintaining the substrate in contact with the alkali solution obtained in step (b) to form a carbonated hydroxyapatite coating, and (d) taking the substrate off the solution and subjecting the coating to drying. The bicarbonate ions are disclosed to act as inhibitors of hydroxyapatite crystal growth, resulting in non-stoichiometric crystals containing defects and having rather small dimensions, namely 10-40 nm in length and 3-10 nm in width (see page 7, lines 1-7).

The components of calcium phosphate/hydroxyapatite (CAP/HAP) systems, especially TCP/HAP systems differ in their thermodynamic stability. Due to this difference, when CAP/HAP systems are implanted into a mammal, in particular a human patient, the solubility of TCP and other calcium phosphates is higher in the body fluid than the solubility of HAP. The difference in solubility between calcium phosphates and HAP causes a breakdown of the unordered sinterstructure of the CAP/HAP system because the better soluble compound CAP (e.g. TCP) is removed quicker than HAP. The sintered interconnection between CAP and HAP produced at high temperatures will also make a remarkable contribution to higher solubility of the device in the physiological environment. Two different types of reactions dominate accelerated in vivo degradation of such ceramics: Chemical dissolution and biological resorption by cells. Both processes cause dissolution of the ceramic material which furthermore causes a local oversaturation of calcium ions, whereby there are more calcium ions released than calcium ions adsorbed. The natural equilibrium of calcium ions no longer exists, neither in the extracellular matrix nor in the tissue surrounding of the implant. The local disturbance of the natural calcium equilibrium in terms of oversaturation of calcium ions leads to an increased osteoclast activity and therefore to an accelerated ill-controlled resorption of the ceramic material and a risk of adverse inflammation reactions, especially when using a large amount of synthetic bone substitute material.

When bone substitute material Geistlich Bio-Oss® is implanted into a human patient, the natural calcium equilibrium is practically not affected, the concentration of calcium ions on the surface of the material and within the local environment thereof remaining almost constant. Biological resorption of the material hence does not take place or proceeds at a very slow rate without the risk of adverse inflammation reactions.

EP-B1-2445543 discloses a highly advantageous calcium phosphate/hydroxyapatite (CAP/HAP) bone substitute material which, like bone substitute material Geistlich Bio-Oss®, after being set in vivo enables the concentration of calcium ions on the surface of the material and within the local environment thereof to remain almost constant and thus does not lead to an increased osteoclast activity.

Indeed, the natural calcium equilibrium which is necessary for optimal bone regeneration is not disturbed or destroyed. Moreover, the natural calcium concentration equilibrium is lastingly supported by the bone substitute material until the regeneration process is completed. When those conditions are met there is no increase of osteoclast activity, hence no risk of adverse inflammation reactions.

The invention of EP-B1-2445543 relates to a biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral, i.e. a length of 30 to 46 nm and a width of 14 to 22 nm.

The sintered CAP core may comprise tricalcium phosphate (TCP), notably α-TCP (α-Ca$_3$(PO$_4$)$_2$) or β-TCP (β-Ca$_3$(PO$_4$)$_2$), and/or tetracalcium phosphate (TTCP) Ca$_4$(PO$_4$)$_2$O.

According to a frequently used embodiment the sintered CAP core essentially consists of TCP, α-TCP being preferred.

The epitactically grown layer of nanocrystalline HAP is structurally and chemically nearly identical to the natural human bone mineral.

The epitactically grown layer of nanocrystalline HAP generally has a thickness of at least from 15 to 50 nm, preferably at least from 20 to 40 nm, more preferably at least from 25 to 35 nm. That minimum thickness corresponds to one layer of HAP nanocrystals in epitaxial orientation.

The epitactically grown layer of nanocrystalline HAP may comprise a single or multiple layers of HAP nanocrystals in epitaxial orientation. The thickness of the epitactically grown layer of nanocrystalline HAP, which is related to the number of such layers of HAP nanocrystals in epitaxial orientation, will be selected according to the intended application of the bone substitute material as implant or prosthesis in differently loaded parts of the body. The bone substitute material of that invention is indeed designed to function in vivo as a living-like system progressively transforming the sintered CAP core into hydroxyapatite similar in size and morphology to human bone mineral, the rate of that transformation being dependent on the rate of calcium release by the sintered CAP core, which is to a large extent controlled by the thickness of the epitactically grown layer of nanocrystalline HAP.

The properties of the CAP/HAP bone substitute material are to a large extent controlled by the thickness of the epitactically grown layer of crystalline HAP. The term "properties" includes the ability of the CAP/HAP bone substitute to release a constant concentration of calcium ions to the local environment in vitro and in vivo.

The thickness of the epitactically grown layer of nanocrystalline HAP is related to the ratio of the sintered CAP core material to HAP, said ratio being generally between 5:95 and 95:5, preferably from 10:90 to 90:10.

The CAP/HAP bone substitute material may be a particulate or a granulate, the particles or granules having a desired size and shape. Generally, the particles or granules are approximately spherical and have a diameter of 250 to 5000 µm.

The CAP/HAP bone substitute material may also be a shaped body, e.g. a screw, a nail, a pin or a structure having the profile of an osseous body part such as notably a hip, a clavicle, a rib, a mandible or a skull part. Such a screw, a nail or a pin may be used in reconstructive orthopedic surgery for fixing a ligament to a bone, for example in the knee or the elbow. Such a structure having the profile of an osseous body part may be used in orthopedic surgery as prosthesis for replacing a missing or defective bone or bone part.

That CAP/HAP bone substitute material of EP-B1-2445543 is taught to be obtained by a process comprising the steps of a) preparing a sintered CAP core material, b) immersing the sintered CAP core material in an aqueous solution at a temperature between 10° C. and 50° C. to start the transformation process of CAP to HAP, whereby a uniform and closed epitactically grown layer of nanocrystalline hydroxyapatite is formed on the sintered CAP core material surface, the epitactically grown nanocrystals having the same size and morphology as human bone mineral, c) stopping the transformation by separating the solid material from the aqueous solution at a time when a uniform and closed coating of at least one nanocrystalline layer of HAP is present but before the transformation process is finished completely, d) optionally sterilizing the separated material coming from step c).

The preparation of the sintered CAP core material may be performed by methods known in the art comprising first mixing powders of calcium hydrogen phosphate ($CaHPO_4$), calcium carbonate and/or calcium hydroxide, then calcining and sintering the mixture within an appropriate temperature range, thereby giving a bulk sintered CAP core material (see e.g. Mathew M. et al., 1977, Acta. Cryst. B33: 1325; Dickens B. et al., 1974, J. Solid State Chemistry 10, 232; and Durucan C. et al., 2002, J. Mat. Sci., 37:963).

A bulk sintered TCP core material may thus be obtained by mixing powders of calcium hydrogen phosphate ($CaHPO_4$), calcium carbonate and/or calcium hydroxide in stoichiometric ratio, calcining and sintering the mixture at a temperature in the range of 1200-1450° C., preferably about 1400° C.

A bulk sintered TTCP core material may also be obtained by the above described process.

The bulk sintered CAP material prepared by such methods may be porous with a porosity of 2 to 80 vol % and a wide distribution of pores. The porosity parameters will be selected according to the intended application of the CAP/HAP bone substitute material.

The sintered CAP core material used in step b) may be the bulk sintered CAP core material prepared as described above, a particulate or granulate of sintered CAP core material obtained from the bulk sintered CAP core material prepared as described above, by using conventional methods such as crushing, grinding and/or milling, and sieving, or a preform of sintered CAP core material having a desired shape and size, e.g. a screw, a nail, a pin or a structure having the profile of an osseous body part.

Such a preform of any desired shape and size may be obtained from the bulk sintered core material prepared as described above, by using well known prototyping techniques such as CNC milling or 3D printing (see for example Bartolo P. et al., 2008, Bio-Materials and Prototyping Applications in Medicine, Springer Science New York, ISBN 978-0-387-47682-7; Landers R. et al., 2002, Biomaterials 23(23), 4437; Yeong W.-Y. et al., 2004, Trends in Biotechnology, 22 (12), 643; and Seitz H. et al., 2005, Biomed. Mater. Res. 74B (2), 782).

The aqueous solution of step b) is taught to be pure water, a simulated body fluid or a buffer. Important is that the pH value of the immersing solution of step b) is nearly neutral and remains stable throughout the transformation process, preferably within a pH range from 5.5 to 9.0.

The term "simulated body fluid" refers to any solution that mimics a body fluid. Preferably, the simulated body fluid has an ion concentration similar to that of blood plasma.

The buffer may be any buffer in the above pH range but is preferably a phosphate buffer with or without calcium, magnesium and/or sodium.

The buffer used in the Examples (see Examples 4 and 5) is an aqueous phosphate buffer.

The temperature range in step b) is generally between 10° C. and 50° C., preferably between 25 and 45° C., more preferably between 35° C. and 40° C.

The immersing step b) induces in a first phase a first-order phase transition of the CAP core material and therefore the nucleation of HAP nanocrystal precursors. During the second phase the resulting HAP precursors from the first phase will grow and establish a closed (i.e. completely coating) epitactic nanocrystalline composite layer. The first HAP nanocrystal layer must be uniform and closed and epitaxially connected to the sintered CAP core material.

During a third phase the first-order phase transition may proceed within the newly formed bilayer composite to further transform the sintered CAP core material (TCP or TTCP) into nanocrystalline HAP. During this third step of phase transition calcium ions will be released for a controllable time by a slow diffusion controlled process until a part of the sintered CAP core material has been transformed into nanocrystalline HAP. The thickness of the HAP layer and therefore the rate of calcium release can be controlled by variation of the transformation time.

The epitactically grown nanocrystalline HAP layer of appropriate thickness will be prepared in vitro, the transformation of CAP into HAP being stopped before it is completed.

As soon as the CAP/HAP bone substitute material is set in vivo, the transformation process of CAP into HAP will be reactivated by contact with the body fluids and the bone substitute material will function as a living-like system forming new hydroxyapatite similar in size and morphology to human bone mineral. During the in vivo phase transformation process the transported calcium ions will be released into the local environment supporting the local calcium equilibrium which is important and beneficial for bone regeneration processes.

Due to different regeneration times of bone defects in differently loaded regions of the body it is important that the rate of calcium release can be controlled. This can be achieved by variation of the thickness of the epitactically grown layer of hydroxyapatite.

Step c) is therefore a very critical step. The exposure time in the aqueous solution of step b) is based upon the thickness of the HAP layer desired. At least one layer of nanocrystalline HAP in epitaxial orientation is necessary. It is essential that the transformation of CAP into HAP is not finished.

The proper exposure time according to the thickness desired can be calculated by using several thermodynamic differential equations well known to the skilled person in the art of calcium phosphates, cement and concrete chemistry.

See for example: Pommersheim, J. C.; Clifton, J. R. (1979) Cem. Conc. Res.; 9:765; Pommersheim, J. C.; Clifton, J. R. (1982) Cem. Conc. Res.; 12:765; and Schlüssler, K. H. Mcedlov-Petrosjan, O. P.; (1990): Der Baustoff Beton, VEB Verlag Bauwesen, Berlin.

Transferring the solution of the above mentioned differential equations to the CAP/HAP system enables the prediction of the phase transition of CAP into HAP and the thickness of the layer such that the epitactic layer of HAP can be prepared in a stable and reproducible manner.

Separating the solid material from the aqueous solution at the end of step c) is usually performed by filtration, washing and drying, using techniques well known in the art.

In the Examples of EP-B1-2445543 (namely Example 4 [0057] and Example 5 [0058]), washing is performed by washing the separated granules 3 times with purified water to remove residuals from the buffered solution.

The optional sterilizing step d) may be performed by techniques well known in the art such as gamma-irradiation or X-ray radiation.

Using as taught in Examples 4 and 5 of EP-B1-2445543 an aqueous phosphate buffer for the aqueous solution of step b) and purified water to wash 3 times the separated granules at the end of step c), one obtains a biphasic calcium phosphate/hydroxyapatite (CAP/HAP) bone substitute material comprising a sintered CAP core and a closed epitactically grown layer of nanocrystalline HAP deposited on the external surface of the sintered CAP core, whereby the epitactically grown nanocrystals have the same size and morphology as human bone mineral, i.e. a length of 30 to 46 nm and a width of 14 to 22 nm, wherein the closed epitactically grown layer of nanocrystalline HAP deposited on the external surface of the sintered CAP core has a non-homogeneous external surface comprising individual (separated) clusters of flat crystal platelets consisting of epitactically grown HAP nanocrystals and smooth areas between the individual clusters of flat crystal platelets, the % of the external surface occupied by the smooth areas between the individual clusters of flat crystal platelets depending on the transformation time in given transformation conditions.

See FIG. 1A, which represents a SEM (scanning electron microscopy) picture of prototype 1 (1-2 mm granule) having a transformation time of 30 min wherein the smooth areas represent about 70% of the total external surface as measured by SEM and FIG. 1B, which represents an SEM picture of prototype 2 (1-2 mm granule) having a transformation time of 40 min wherein the smooth areas represent about 50% of the total external surface as measured by SEM.

WO 2015/009154 discloses a method for producing an osteoconductive material with improved osteoinductive capacity, which comprises subjecting a sintered biphasic calcium phosphate/hydroxyapatite (CAP/HAP) material having a surface topography consisting of grains to a hydrothermal treatment under a pressure of 2-4 bars at a temperature equal to or higher than 125° C. without controlling the pH for a duration sufficient to change calcium phosphate grains on the surface of the starting material into calcium phosphate needles of a diameter 10-1500 nm. A temperature of at least 125° C. and a pressure of at least 2 bars is far from the (close to the human body physiological) conditions used in EP-B1-2445543 (temperature 35-40° C., pH 5.5-9.0, ambient pressure) which enable epitactic growth of HAP nanocrystals. Those needles are not epitactically grown but attached to or deposited on the core material base and only partially (usually 40-90%) coat the latter, thereby increasing its specific surface and capacity of harboring proteins, thus enhancing its osteoinductive potential.

It has now been found that by adding 10 to 90%, preferably 20 to 60%, of a short-chain aliphatic alcohol including but not limited to methanol, ethanol, propanol or butanol to the aqueous phosphate buffer of step b) in preparation of the biphasic calcium phosphate/hydroxyapatite (CAP/HAP) bone substitute material according to EP-B1-2445543, the non-homogeneous external surface of the closed epitactically grown layer of nanocrystalline HAP deposited on the external surface of the sintered CAP core biphasic calcium phosphate/hydroxyapatite (CAP/HAP) bone substitute material, which comprises individual clusters of flat crystal platelets and smooth areas in between, is replaced by a homogeneous coarse external surface comprising flat crystal platelets without any individual crystal clusters of flat crystal platelets. That homogeneous coarse external surface generally comprises epitactically grown nanocrystalline hydroxyapatite platelets forming an interlocked network of platelets with individual platelet sizes of 0.2 to 20 µm, preferably 0.5 to 5 µm, as determined by SEM, depending on the amount of aliphatic alcohol used.

As shown by in vitro tests of osteogenic differentiation of fetal human mesenchymal stem cells (hMSCs), the in vivo osteogenic response is likely to be stronger for the biphasic calcium phosphate/hydroxyapatite (CAP/HAP) bone substitute material having that homogeneous coarse external surface comprising flat crystal platelets than for the biphasic calcium phosphate/hydroxyapatite (CAP/HAP) bone substitute material taught by EP-B1-2445543 which has a non-homogeneous external surface comprising individual clusters of flat crystal platelets and smooth areas in between.

SUMMARY OF THE INVENTION

The invention thus concerns a biphasic calcium phosphate/hydroxyapatite (CAP/HAP) bone substitute material comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a homogeneous coarse external surface comprising flat crystal platelets.

That biphasic calcium phosphate/hydroxyapatite (CAP/HAP) bone substitute material shows an increased osteogenic differentiation of fetal human mesenchymal stem cells (hMSCs), which is a strong indication of an enhanced in vivo osteogenic response.

The term "closed epitactically grown layer of nanocrystalline HAP deposited on the external surface of the sintered CAP core" means that the epitactically grown layer of nanocrystalline HAP completely covers the entire external surface of the sintered CAP core.

The term "homogeneous coarse external surface comprising flat crystal platelets" means that macroscopically the coarseness of the external surface caused by the flat crystal platelets is statistically evenly distributed on the surface of the CAP core without individual crystal clusters of flat crystal platelets. See FIG. 2 which represents SEM pictures of prototypes 3 to 7 of the biphasic calcium phosphate/hydroxyapatite (CAP/HAP) bone substitute material of the invention with a homogeneous coarse external surface with a varying degree of coarseness.

The term "flat crystal platelets" means crystal assemblies where the height (thickness) is considerably smaller than the width and length with respect to the three perpendicular directions. Such flat crystal platelets are clearly visible in FIG. 3B.

Generally, the homogeneous coarse external surface comprises epitactically grown nanocrystalline hydroxyapatite platelets forming an interlocked network of platelets with sizes (width and length) of 0.2 to 20 µm as determined by SEM. The larger the sizes of the platelets, the higher the coarseness of the external surface.

Preferably, the homogeneous coarse external surface comprises epitactically grown nanocrystalline hydroxyapatite platelets forming an interlocked network of platelets with sizes of 0.5 to 5 µm as determined by SEM Usually, that homogeneous coarse external surface comprises epitactically grown hydroxyapatite platelets forming an interlocked network containing pores between 0.03 and 2 µm as determined by Mercury Intrusion Porosimetry (MIP). The higher the pore volume between 0.03 and 2 µm is, the higher is the coarseness of the external surface.

Generally, that homogeneous coarse external surface may be characterized by AFM (Atomic Force Microscopy) with an AFM-derived root mean square roughness ($R_q$) in a range of 50 to 400 nm and an average maximum height of the profile ($R_z$) in a range of 500 to 2000 nm.

Preferably, the homogeneous coarse external surface may be characterized by an AFM-derived root mean square roughness ($R_q$) in a range of 110 to 150 nm and an average maximum height of the profile ($R_z$) in a range of 550 to 750 nm.

Generally, the percentage of HAP in the biphasic calcium phosphate/hydroxyapatite (CAP/HAP) bone substitute material is from 1 to 90%, as measured by XRD.

Preferably, that percentage is from 1.5 to 30%, more preferably from 2 to 15%, as measured by XRD.

The sintered CAP core comprises tricalcium phosphate (TCP), notably α-TCP ($\alpha$-$Ca_3(PO_4)_2$) or β-TCP ($\beta$-$Ca_3(PO_4)_2$), and/or tetracalcium phosphate (TTCP) $Ca_4(PO_4)_2O$.

According to a frequently used embodiment the sintered CAP core essentially consists of TCP, α-TCP being preferred.

The epitactically grown layer of nanocrystalline HAP is structurally nearly identical to the natural human bone mineral.

The CAP/HAP bone substitute material may be a particulate or a granulate, the particles or granules having a desired size and shape. Generally, the particles or granules have a size of 250 to 5000 µm, preferably 1000 to 2000 µm.

The CAP/HAP bone substitute material may also be a shaped body, e.g. a screw, a nail, a pin or a structure having the profile of an osseous body part such as notably a hip, a clavicle, a rib, a mandible or a skull part. Such a screw, a nail or a pin may be used in reconstructive orthopedic surgery for fixing a ligament to a bone, for example in the knee or the elbow. Such a structure having the profile of an osseous body part may be used in orthopedic surgery as prosthesis for replacing a missing or defective bone or bone part.

The invention also relates to a putty comprising particles or granules of the above defined CAP/HAP bone substitute in a suitable matrix, generally comprising natural or synthetic polymers. Generally, the particles or granules have a size of 250 to 5000 µm, preferably 1000 to 2000 µm.

The invention further relates to a process of preparing the above defined CAP/HAP bone substitute material comprising the steps of
 a) preparing a sintered CAP core material,
 b) immersing the sintered CAP core material in a buffer solution containing 10 to 90% of a short-chain aliphatic alcohol at a temperature between 10° C. and 50° C. to start the transformation process of CAP to HAP whereby a closed epitactic grown layer of nanocrystalline hydroxyapatite will be formed on the sintered CAP core material surface, whereby the epitactically grown nanocrystals have the same size and morphology as human bone mineral, wherein the closed epitactically grown layer of nanocrystalline HAP formed on the sintered CAP core material surface has a homogeneous external surface comprising flat crystal platelets,
 c) stopping the transformation by separating solid material from the aqueous solution at a time when a closed coating of at least one nanocrystalline layer of HAP is present but before the transformation process is finished completely, and
 d) optionally sterilizing the separated material coming from step c).

A suitable short-chain aliphatic alcohol may be selected from the group consisting of methanol, ethanol, propanol and butanol.

Preferably the short-chain aliphatic alcohol is ethanol.

Preferably, the buffer solution of step b) contains 20 to 60%, more preferably 30 to 50%, of a short-chain aliphatic alcohol.

The coarseness parameters of the homogeneous coarse external surface of the closed epitactically grown layer of nanocrystalline HAP deposited on the external surface of the sintered CAP core, notably
- the AFM parameters: the AFM-derived root mean square roughness ($R_q$) and the average maximum height of the profile ($R_z$),
- the sizes of the epitactically grown nanocrystalline hydroxyapatite platelets as determined by SEM and
- the volume of pores between 0.03 and 2 μm as determined by MIP can conveniently be adjusted by changing the percentage of the short-chain aliphatic alcohol in the buffer solution of the transformation solution.

The higher that percentage is, the lower are the AFM-derived root mean square roughness ($R_q$) and the average maximum height of the profile ($R_z$), the smaller are the sizes of the epitactically grown nanocrystalline hydroxyapatite platelets as determined by SEM and the smaller is the volume of pores between 0.03 and 2 μm as determined by MIP.

The buffer solution of step b) containing 10 to 90% of a short-chain aliphatic alcohol is obtained by mixing an aqueous buffer solution with varying amounts of a short-chain aliphatic alcohol. The aqueous buffer solution is chosen such that the pH value of the immersing solution of step b) which further contains 10 to 90% of a short-chain aliphatic alcohol is nearly neutral and remains stable throughout the transformation process, preferably within a pH range from 5.5 to 9.0, more preferably from 7.0 to 8.0.

The buffer may be any buffer in the above pH range but is preferably a phosphate buffer with or without calcium, magnesium and/or sodium.

A suitable buffer solution is e.g. a 0.05-0.3 M aqueous solution of sodium dihydrogen phosphate ($NaH_2PO_4$) with a pH value of 7.3 to 7.6.

The temperature range in step b) is generally between 10° C. and 50° C., preferably between 25 and 45° C., more preferably between 35° C. and 40° C.

Preferably step b) is carried out at a temperature of 35 to 40° C. in a phosphate buffer solution of pH from 7.0 to 8.0 containing 20 to 60% of a short-chain aliphatic alcohol.

The preparation of the sintered CAP core material may be performed by methods known in the art comprising first mixing powders of calcium hydrogen phosphate ($CaHPO_4$), calcium carbonate and/or calcium hydroxide, then calcining and sintering the mixture within an appropriate temperature range, thereby giving a bulk sintered CAP core material (see e.g. Mathew M. et al., 1977, Acta. Cryst. B33: 1325; Dickens B. et al., 1974, J. Solid State Chemistry 10, 232; and Durucan C. et al., 2002, J. Mat. Sci., 37:963).

A bulk sintered TCP core material may thus be obtained by mixing powders of calcium hydrogen phosphate ($CaHPO_4$), calcium carbonate and/or calcium hydroxide in stoichiometric ratio, calcining and sintering the mixture at a temperature in the range of 1200-1450° C., preferably about 1400° C.

A bulk sintered TTCP core material may also be obtained by the above described process.

The bulk sintered CAP material prepared by such methods may be porous with a porosity of 2 to 80 vol % and a wide distribution of pores. The porosity parameters will be selected according to the intended application of the CAP/HAP bone substitute material.

The sintered CAP core material used in step b) may be
- the bulk sintered CAP core material prepared as described above,
- a particulate or granulate of sintered CAP core material obtained from the bulk sintered CAP core material prepared as described above, by using conventional methods such as crushing, grinding and/or milling, and sieving, or
- a preform of sintered CAP core material having a desired shape and size, e.g. a screw, a nail, a pin or a structure having the profile of an osseous body part.

Such a preform of any desired shape and size may be obtained from the bulk sintered core material prepared as described above, by using well known prototyping techniques such as CNC milling or 3D printing (see for example Bartolo P. et al., 2008, Bio-Materials and Prototyping Applications in Medicine, Springer Science New York, ISBN 978-0-387-47682-7; Landers R. et al., 2002, Biomaterials 23(23), 4437; Yeong W.-Y. et al., 2004, Trends in Biotechnology, 22 (12), 643; and Seitz H. et al., 2005, Biomed. Mater. Res. 74B (2), 782).

The immersing step b) induces in a first phase a first-order phase transition of the CAP core material and therefore the nucleation of HAP nanocrystal precursors. During the second phase the resulting HAP precursors from the first phase will grow and establish a closed (i.e. completely coating) epitactic nanocrystalline composite layer. The first HAP nanocrystal layer must be uniform and closed and epitactically connected to the sintered CAP core material.

During a third phase the first-order phase transition may proceed within the newly formed bilayer composite to further transform the sintered CAP core material (TCP or TTCP) into nanocrystalline HAP. During this third step of phase transition calcium ions will be released for a controllable time by a slow diffusion controlled process until a part of the sintered CAP core material has been transformed into nanocrystalline HAP. The thickness of the HAP layer and therefore the rate of calcium release can be controlled by variation of the transformation time.

The epitactically grown nanocrystalline HAP layer of appropriate thickness will be prepared in vitro, the transformation of CAP into HAP being stopped before it is completed.

As soon as the CAP/HAP bone substitute material is set in vivo the transformation process of CAP into HAP will be reactivated by contact with the body fluids and the bone substitute material will function as a living-like system forming new hydroxyapatite similar in size and morphology to human bone mineral.

During the in vivo phase transformation process the transported calcium ions will be released into the local environment supporting the local calcium equilibrium which is important and beneficial for bone regeneration processes.

Due to different regeneration times of bone defects in differently loaded regions of the body it is important that the rate of calcium release can be controlled. This can be achieved by variation of the thickness of the epitactically grown layer of hydroxyapatite.

Step c) is therefore a very critical step. The exposure time in the aqueous solution of step b) is based upon the thickness of the HAP layer desired. At least one layer of nanocrystalline HAP in epitaxial orientation is necessary. It is essential that the transformation of CAP into HAP is not finished.

The proper exposure time according to the thickness desired can be calculated by using several thermodynamic differential equations well known to the skilled person in the art of calcium phosphates and cement and concrete chemistry.

See for example: Pommersheim, J. C.; Clifton, J. R. (1979) Cem. Conc. Res.; 9:765; Pommersheim, J. C.; Clifton, J. R. (1982) Cem. Conc. Res.; 12:765; and Schlüssler, K. H. Mcedlov-Petrosjan, O. P.; (1990): Der Baustoff Beton, VEB Verlag Bauwesen, Berlin.

Transferring the solution of the above mentioned differential equations to the CAP/HAP system enables the prediction of the phase transition of CAP into HAP and the thickness of the layer such that the epitactic layer of HAP can be prepared in a stable and reproducible manner.

Separating the solid material from the aqueous solution is usually performed by filtration and drying, using techniques well known in the art.

The optional sterilizing step d) may be performed by techniques well known in the art such as gamma-irradiation or X-ray radiation.

The invention also concerns the use of the above defined CAP/HAP bone substitute material, generally in the form of a particulate, a putty or a shaped body as an implant or prosthesis for supporting bone formation, bone regeneration, bone repair and/or bone replacement at a defect site in a human or animal.

The invention also relates to a method of promoting bone formation, bone regeneration and/or bone repair at a defect site in a human or animal by implanting the above defined CAP/HAP bone substitute material, generally in the form of a particulate, a putty or a shaped body.

Advantages of the CAP/HAP Bone Substitute Material of the Invention and the Process of Preparation Thereof.

That biphasic calcium phosphate/hydroxyapatite (CAP/HAP) bone substitute material of the invention with a homogeneous coarse external surface comprising flat crystal platelets shows an increased osteogenic differentiation of fetal human mesenchymal stem cells (hMSCs), in particular a higher expression of differentiation markers osteopontin (OPN) and osteocalcin (OCN), compared with the biphasic calcium phosphate/hydroxyapatite (CAP/HAP) bone substitute material taught by EP-B1-2445543 which has a non-homogeneous external surface comprising individual clusters of flat crystal platelets and smooth areas in between. This is a strong indication of an enhanced in vivo osteogenic response.

This is in line with the results published by R. A. Gittens et al. in Biomaterials 2011 May, 32(13): 3395-3403, which show that the introduction of nanoscale structures in combination with micro-submicro-scale roughness improves osteoblast differentiation and local factor production, which in turn indicates the potential for improved implant osseointegration in vivo.

The process of preparation of the biphasic calcium phosphate/hydroxyapatite (CAP/HAP) bone substitute material of the invention allows to conveniently adjust the coarseness parameters of the homogeneous coarse external surface of the closed epitactically grown layer of nanocrystalline HAP deposited on the external surface of the sintered CAP core, notably the AFM parameters: AFM-derived root mean square roughness ($R_q$) and average maximum height of the profile ($R_z$),
the sizes of the epitactically grown nanocrystalline hydroxyapatite platelets as determined by SEM and
the volume of pores between 0.03 and 2 μm as determined by MIP, by adjusting the percentage of the short-chain aliphatic alcohol in the buffer solution of the transformation solution.

The higher that percentage is, the lower are the AFM-derived root mean square roughness ($R_q$) and the average maximum height of the profile ($R_z$), the smaller are the sizes of the epitactically grown nanocrystalline hydroxyapatite platelets as determined by SEM and the smaller is the volume of pores between 0.03 and 2 μm as determined by MIP.

BRIEF DESCRIPTION OF THE DRAWINGS

The invention will be described in further detail hereinafter with reference to illustrative examples of preferred embodiments of the invention and the accompanying drawing figures, in which.

All SEM pictures of FIG. 1 and FIGS. 2A-2E have a magnification of 3500.

Figure 3A:
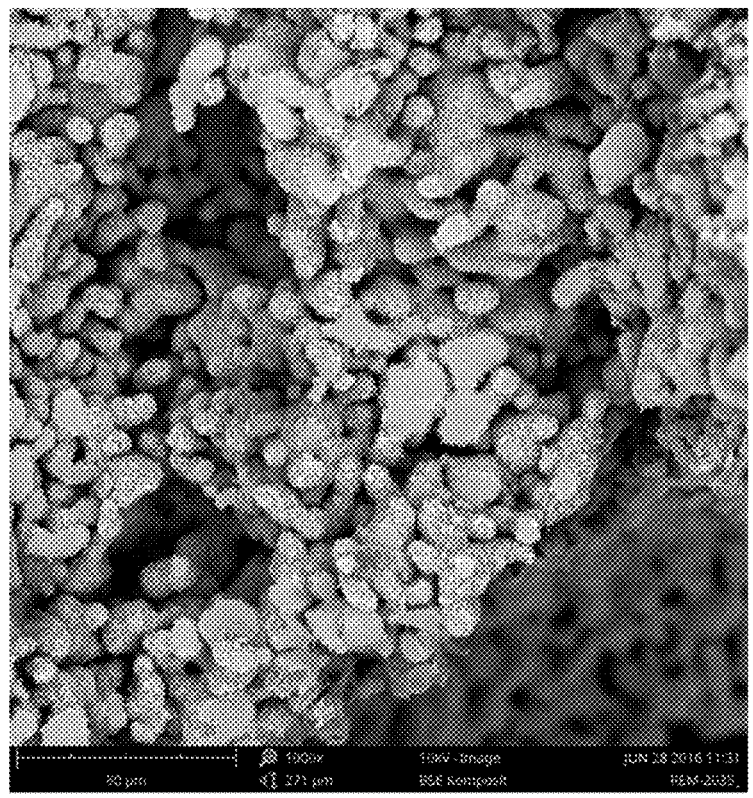

FIG. 3A represents a SEM picture of a cross-section of prototype 5 (40% ethanol, 1-2 mm granule) at low magnification (1000×). The bottom-right corner shows the outer surface of the granule and the center of the granule is located towards the top-left corner.

Figure 3B:
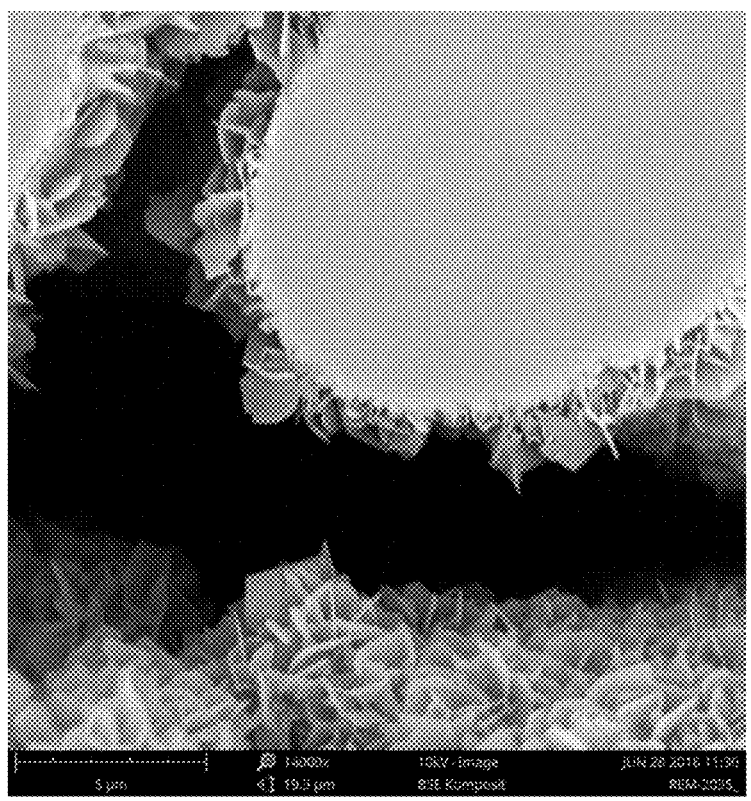

FIG. 3B represents a SEM picture of a cross-section of prototype 5 (40% ethanol, 1-2 mm granule) at higher magnification (14'000×).

Figure 4:
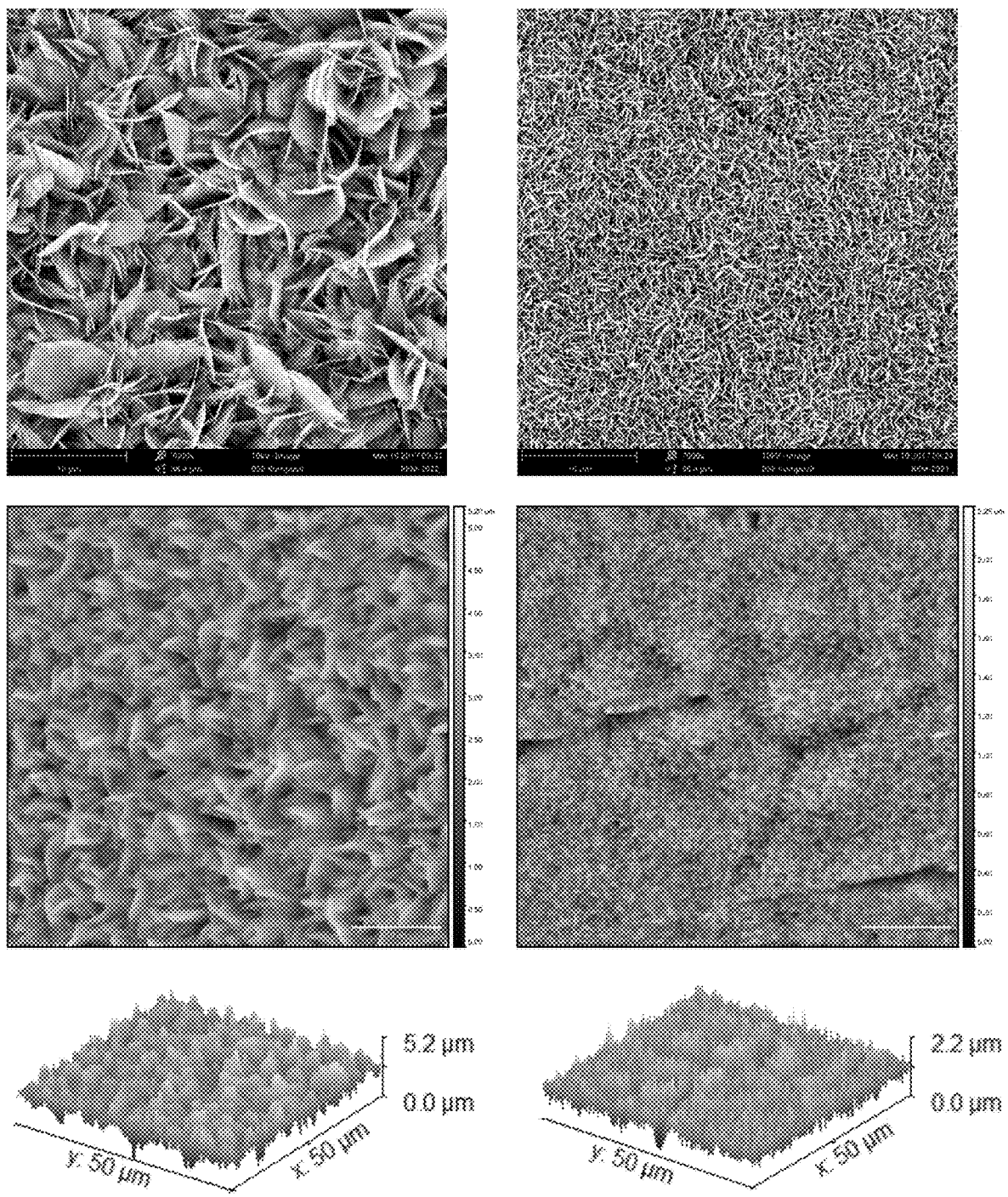

FIG. 4 represents SEM pictures (the two upper pictures) and AFM pictures (the other four pictures) of prototypes 3a (left: 20% ethanol) and 6a (right: 50% ethanol) of non-porous discs of bone substitute materials according to the invention prepared in Example 2.

Figures 5A, 5B:
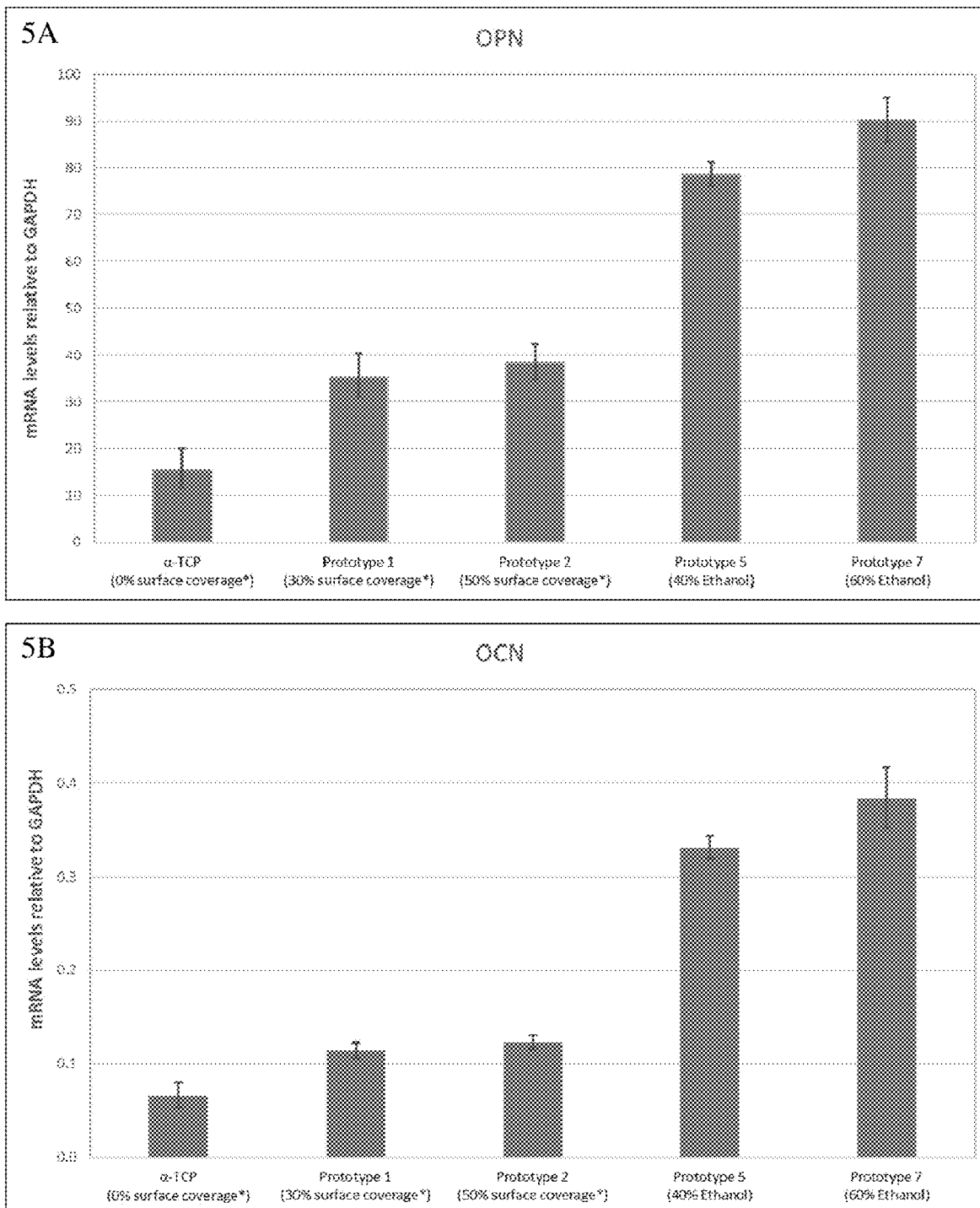

FIGS. 5A-5B represent the osteocalcin (OCN, FIG. 5A) and the osteopontin (OPN, FIG. 5B) responses of fetal human mesenchymal stem cells (hMSCs) in contact with bone substitute materials according to the invention compared to prior art bone substitute materials in an in vitro test.

Figure 6:
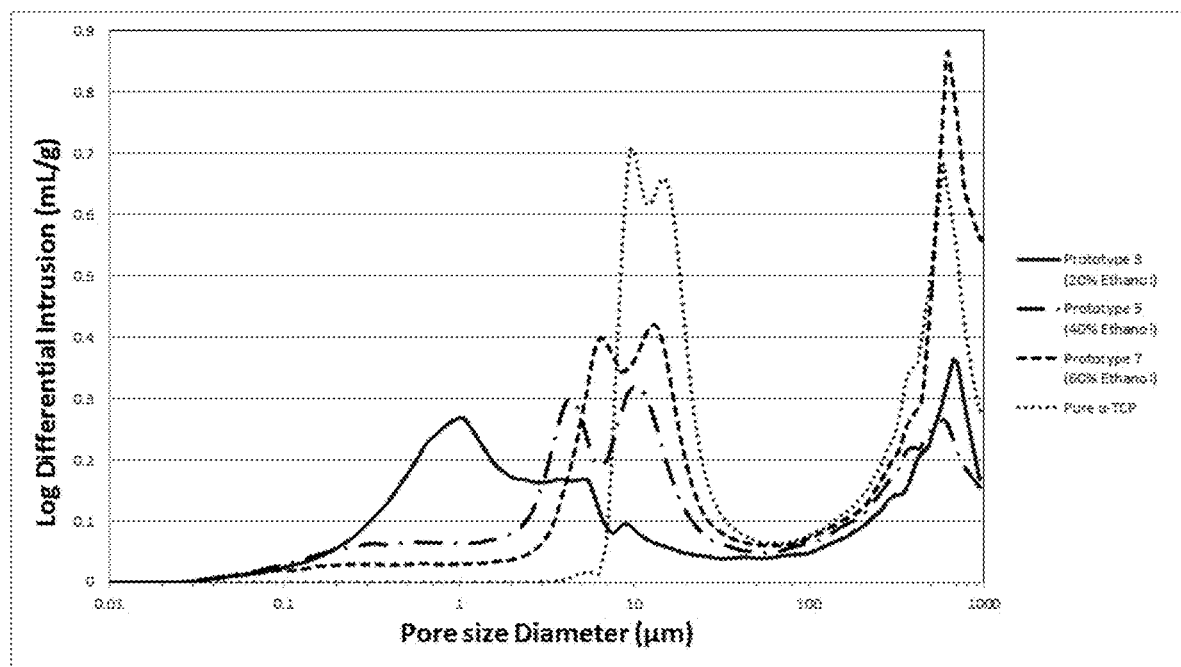

FIG. 6 represents MIP diagrams of 1-2 mm granules of prototypes 3 (20% ethanol), 5 (40% ethanol) and 7 (60% ethanol) of the 1-2 mm granules of bone substitute materials according to the invention prepared in Example 2 and pure α-TCP produced as described in Example 1.

DETAILED DESCRIPTION

The following examples illustrate the invention without limiting its scope.

Example 1 Preparation of Biphasic Calcium Phosphate/Hydroxyapatite (CAP/HAP) Bone Substitute Materials According to EP-B1-2445543

A bulk sintered material of alpha-TCP, porous granules thereof with a particle size of 1.0-2.0 mm and transformed granules having an epitactically grown HAP coating were prepared similarly to Examples 1, 2 and 4 of EP-B1-2445543.

364 g dicalcium phosphate anhydrous powder, 136 g calcium carbonate powder and 220 ml deionized water were mixed for 5 min at 700 rpm using a laboratory stirrer. The slurry from the mixing process was immediately transferred into a high temperature stable platinum cup. The filled platinum cup was placed in a cold furnace. The furnace was heated to 1400° C. by using a heating rate of 100° C. per hour. This temperature was kept for 12 hours and afterwards the furnace was cooled down to 800° C. with a cooling rate of 500° C. per hour, then cooled down to 300° C. with a cooling rate of 125° C. per hour and finally cooled down to room temperature by switching of the furnace. The bulk sintered material (phase pure $\alpha\text{-}Ca_3(PO_4)_2$) was removed from the furnace and the platinum cup. The control of phase purity was performed using powder X-ray diffraction analysis.

The bulk product was crushed by using a jaw crusher (jaw distances varied from 10 to 1 mm). The produced granules were sieved by using a sieving machine and sieve inserts with mesh apertures of 2 mm and 1 mm. After sieving, the granules were rinsed with ethanol for separating fine powder residuals adsorbed to the granules. The porous granules were dried for 1 h at 80° C. in a cabinet dryer. The cleanness of the particle surfaces after rinsing was controlled by surface observation using scanning electron microscopy.

A buffered solution adequate for the coating and phase transformation process was prepared by dissolving 0.4 mol/l sodium dihydrogen phosphate ($NaH_2PO_4$) in distilled water. The pH of the solution was adjusted to 7.45 at room temperature by using sodium hydroxide (NaOH). The granules produced according to the previous paragraphs were immersed into the prepared solution and stored within a well-tempered water bath (40° C.) for 30 min (prototype 1) respectively 40 min (prototype 2). After immersing, the granules were rinsed 3 times with distilled water to stop the phase transformation process and remove residuals from the buffered solution. The porous granules were dried at 100° C. in a cabinet dryer for 2 hours.

SEM with a magnification of 3500× was performed on granules of prototype 1 and prototype 2.

Figure 1A:
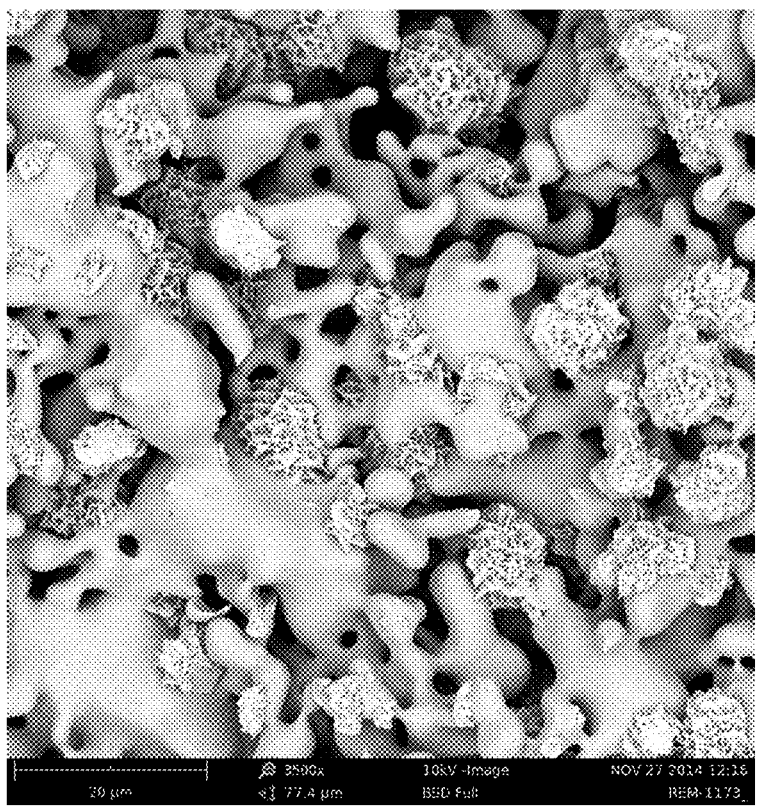
FIG. 1A represents an SEM picture of prototype 1 (1-2 mm granule) of a bone substitute material disclosed by EP-B1-2445543 and prepared in Example 1 having a transformation time of 30 min wherein the smooth areas represent about 70% of the total external surface as measured by SEM.
Figure 1B:
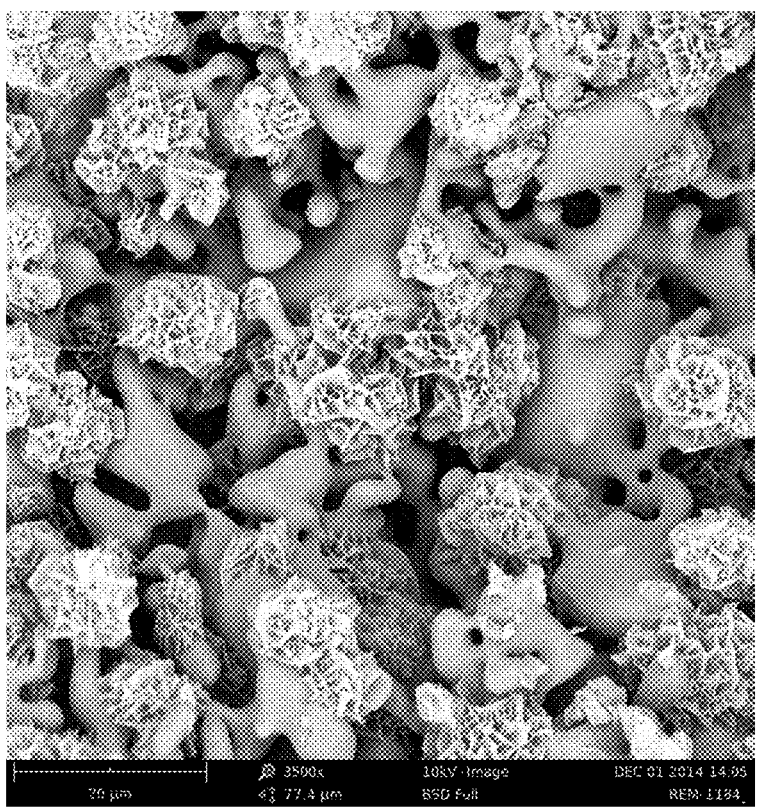
FIG. 1B which represents an SEM picture of prototype 2 (1-2 mm granule) of a bone substitute material disclosed by EP-B1-2445543 and prepared in Example 1 having a transformation time of 40 min wherein the smooth areas represent about 50% of the total external surface as measured by SEM.
Figures 2A, 2B, 2C, 2D, 2E:
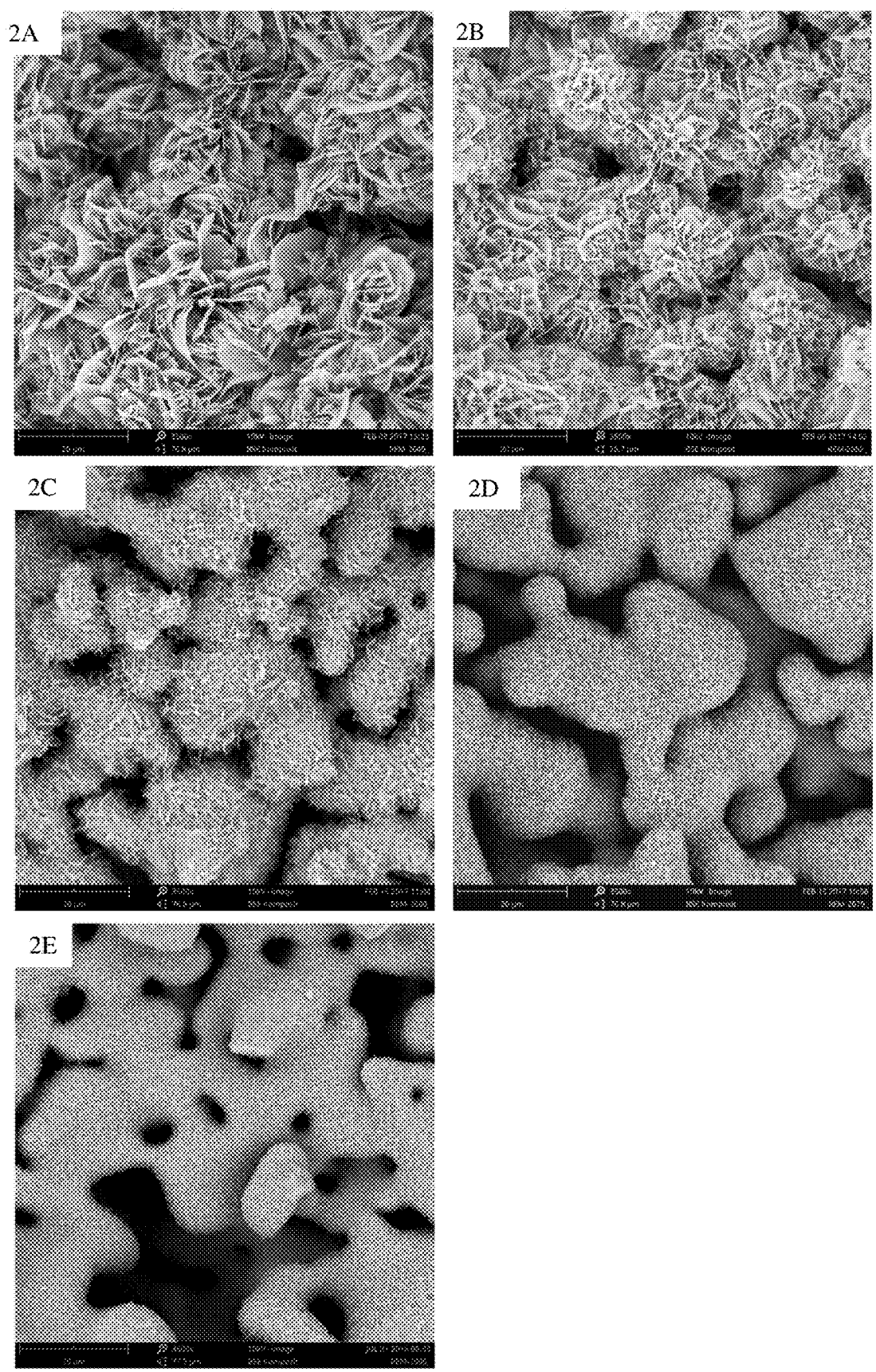
FIGS. 2A-2E represent SEM pictures of prototype 3 (FIG. 2A): 20% ethanol, 1-2 mm granule), prototype 4 (FIG. 2B): 30% ethanol, 1-2 mm granule), prototype 5 (FIG. 2C): 40% ethanol, 1-2 mm granule), prototype 6 (FIG. 2D): 50% ethanol, 1-2 mm granule) and prototype 7 (FIG. 2E): 60% ethanol, 1-2 mm granule) of bone substitute materials according to the invention.

As apparent from FIGS. 1A and 1B, which represent SEM pictures of prototypes 1 and 2, the external surface of the granules is non-homogeneous comprising individual (separated) clusters of flat crystal platelets consisting of epitactically grown HAP nanocrystals and smooth areas between the crystals.

By measuring the surface occupied by the individual clusters and the smooth areas on the SEM pictures for each of prototype 1 and prototype 2, it was determined that the smooth areas represent about 70% of the external surface for prototype 1 and about 50% of the external surface for prototype 2.

Example 2 Preparation of Biphasic Calcium Phosphate/Hydroxyapatite (CAP/HAP) Bone Substitute Materials According to the Invention 1) Preparation of Granules of Bone Substitute Material 1-2 mm sized porous granules of phase pure $\alpha$-TCP were produced as described in above Example 1.

The phase transformation and coating step was performed in glass flasks placed in a water bath set to 40° C. The transformation buffer was an aqueous solution of sodium dihydrogen phosphate ($NaH_2PO_4$) mixed with different proportions of ethanol. The molarity of the aqueous solution of sodium dihydrogen phosphate was varied between 0.05 M and 0.3M and the content of ethanol between 20 and 60 w/w %. The pH of the transformation solution was between 7.3 and 7.6.

The glass flasks were filled with the transformation buffer and alpha-TCP granules were added with a ratio between 1:40 to 1:80 (granules to transformation solution). The granules were immersed in the transformation solution at 40° C. for a period between 24 and 72 hours. After immersing, the granules were rinsed 5 times with deionised water (granules to water ratio being 1:10 with respect to weight) and 2 times with Ethanol (99.9%, granules to ethanol ratio being 1:10 with respect to weight) to stop the phase transformation process and remove residuals from the buffered solution. The porous granules were dried at 100° C. in a cabinet dryer for 2 hours.

The surface morphology after the coating and phase transformation process was observed using SEM.

FIG. 2 represents SEM pictures with a 3500× magnification of prototype 3 (20% ethanol), prototype 4 (30% ethanol), prototype 5 (40% ethanol), prototype 6 (50% ethanol) and prototype 7 (60% ethanol) of bone substitute materials according to the invention. It can be seen by comparing FIGS. 1A and 1B to FIG. 2, that the non-homogeneous external surface of prototypes 1 and 2 with the individual clusters of flat crystal platelets and smooth areas in between is replaced by a homogeneous coarse external surface without any individual crystal clusters. The homogeneous coarse external surface is built up of an interlocked network of epitactically grown hydroxyapatite platelets. The individual platelet sizes are decreased by increasing the ethanol content in the transformation solution as observed by the SEM analysis thus decreasing the coarseness or roughness of the external surface.

FIG. 3A represents a SEM picture of a cross-section of prototype 5 (40% ethanol, 1-2 mm granule) at low magnification (1000×). The bottom-right corner shows the outer surface of the granule and the center of the granule is located towards the top-left corner.

FIG. 3B represents a SEM picture of a cross-section of prototype 5 (40% ethanol, 1-2 mm granule) at higher magnification (14'000×) where one can clearly see the individual flat crystal platelets which are the building blocks of the coarse surface. There is no difference between the coarse external surface in the center of the granule and the coarse external surface on the outer surface of the granule.

Determination of the Pore Size Distribution by Mercury Intrusion Porosimetry (MIP)

The pore size distribution of the granules was determined using mercury intrusion porosimetry (MIP). MIP is a standard characterization technique used to determine the pore size distribution of porous materials. The technique is well known in the art and is for example described in Gregg, S. J. and Sing, K. S. W., Adsorption, Surface Area and Porosity, 2nd ed., Academic Press Inc. (1982), 173-190.

FIG. 6 represents MIP diagrams of prototypes 3, 5 and 7 of bone substitute materials according to the invention compared to pure α-TCP (produced according to example 1 and core material of the prototypes 3, 5 and 7). All measurements were performed with 1-2 mm granules.

It can be seen that the pure α-TCP sample does not have any pores in the range of 0.03 to 2 μm because of its smooth surface. All the bone substitute materials according to the invention contain pores in the range of 0.03 to 2 μm due to the porous nature of the homogeneous coarse external surface which is built up of an interlocked network of epitactically grown hydroxyapatite platelets. The pore volume of the coarse external surface, which corresponds to the area under the MIP curve in the range of 0.03 to 2 μm, depends on the individual platelet sizes of the interlocked network. The bigger the individual platelets are, the higher is the included pore volume of the interlocked network. Thus, the included pore volume of the interlocked network can directly be correlated to the coarseness of the surface. The higher the pore volume in the range of 0.03 to 2 μm in the MIP diagram is, the higher is the coarseness of the surface. Prototype 3 has the largest pore volume (area under the curve) in the range of 0.03 to 2 μm of the shown prototypes, followed by prototype 5 and 7. It is confirmed by the SEM analysis in FIGS. 2A-2E that the coarseness of the prototypes is decreasing from prototype 3 to prototype 5 and 7.

2) Preparation of Non-Porous Discs of Bone Substitute Material

The 1-2 mm sized granules of phase pure α-TCP produced as described in above Example 1 were milled with a planetary mill during 20 hours with 150 rpm to obtain a fine powder. The fine powder was filled in a pressing mold and compacted with a hand press with a load of 1 ton. The green body was removed from the mold and transferred to a high temperature furnace. The furnace was heated to 1450° C. by using a heating rate of 250° C. per hour. This temperature was kept for 24 hours and afterwards the furnace was cooled down to 800° C. with a cooling rate of 500° C. per hour and then cooled down to room temperature with a cooling rate of 150° C. per hour. The bulk sintered non-porous material (phase pure α-$Ca_3(PO_4)_2$) was removed from the furnace. The control of phase purity was performed using powder X-ray diffraction analysis and the surface characteristics were analysed by using SEM.

The phase transformation and coating of the prepared discs was performed as described above under 1), with the only difference that the weight ratio of α-TCP to transformation solution was 1 to 3.5.

Prototypes 3a (20% ethanol) and 6a (50% ethanol) of bone substitute materials according to the invention were thus prepared.

The surface morphology after the coating and phase transformation process was observed using SEM. The corresponding roughness parameters were determined using atomic force microscopy AFM.

The SEM images in FIG. 4 confirm that the morphology of the homogeneous coarse external surface of the non-porous discs is identical to the coarse external surface of the granules produced with the corresponding ethanol content from Example 2 paragraph 1 (prototypes 3 and 3a and prototypes 6 and 6a).

Atomic Force Microscopy (AFM)

Surface measurements at the nanoscale were evaluated using atomic force microscopy (TT-AFM, AFM Workshop) in tapping mode. AFM analyses were conducted under ambient atmosphere using non-porous cylindrical discs with a diameter of 11 mm and a height of 1 mm. A resonance frequency of 190 kHz and a tip radius of up to 10 nm were used. Each AFM analysis was performed over a 50 μm×50 μm area and three samples of every group were scanned. The original data was plane-leveled to remove tilt by applying a numerical correction and mean values of root mean square roughness ($R_q$) and average maximum height of the profile ($R_z$) were determined using the Gwyddion software.

A similar surface characterization of the surface is for example described in US-2013-0045360-A1.

FIG. 4 represents AFM pictures of the prototypes 3a (20% ethanol, left hand side) and 6a (50% ethanol, right hand side) of non-porous discs prepared according to the invention. The AFM-derived roughness values for the prototypes 3a and 6a can be found in following Table 1.

TABLE 1

| AFM derived roughness values for prototypes 3a and 6a. | | |
|---|---|---|
| | $R_q$ [nm] | $R_z$ [nm] |
| Prototype 3a (20% Ethanol) | 237 ± 31 | 1391 ± 194 |
| Prototype 6a (50% Ethanol) | 130 ± 13 | 630 ± 82 |

As seen in Table 1, the mean value of the root mean square roughness ($R_q$) decreased from 237 nm to 130 nm and the average maximum height of the profile ($R_z$) decreased from 1391 nm to 630 nm by increasing the ethanol content from 20% to 50%.

Example 3 In Vitro Test of Osteogenic Differentiation of Fetal Human Mesenchymal Stem Cells (hMSCs)

To assess if the bone substitute material prototypes prepared in Examples 1 and 2 support osteogenic differentiation, about 200'000 hMSCs isolated from a human fetal femur after 22 weeks of gestation (commercially available from ScienCell: Cat #7500, Lot #6890) were seeded on 320 mg granules of those bone substitution material prototypes and cultivated for three weeks. The first seven days of culture the commercially available hMSCs expansion medium (MSCM Medium, Cat #7501, ScienCell) was used to optimally support cell proliferation. For the following 14 days the medium was changed to DMEM complemented with 10% FBS and Penicillin/Streptomycin. No additional osteogenic agents were added to the cell culture medium. After three weeks of hMSCs cultivation, total mRNA was isolated, transcribed into cDNA and Real Time Quantitative PCR was performed. The gene expression was calculated after the ΔΔCT method (see Livak K. J. and Schmittgen T. D., Analysis of relative gene expression data using real time quantitative PCR and the 2-ΔΔCT method, 2001, Methods 25, pp. 402-408) using GAPDH as a house-keeping gene. The expression of the osteogenic differentiation markers osteopontin (OPN) and osteocalcin (OCN) was measured for all bone substitute material prototypes in granular form (1-2 mm) prepared in Examples 1 and 2.

Those measurements showed a significantly higher expression of osteogenic differentiation markers OPN and OCN for the bone substitute material prototypes according to the invention of Example 2 than for the prior art bone substitute material prototypes of Example 1 (see FIGS. 5A-5B).

Based on this in vitro results an enhanced osteogenic response for the bone substitute material prototypes according to this invention is to be expected in vivo.

Example 4 Comparison of the Crystal Size and Morphology for the HAP Nanocrystals of the Biphasic CAP/HAP Bone Substitute Material of the Invention and Human Bone Mineral Crystal size analysis was performed by using as in EP-B1-2445543 a refinement of X-ray diffraction data by applying the Bragg method on samples of prototype 3 and on natural human bone mineral.

It was thus shown that the biphasic CAP/HAP bone substitute material of the invention and human bone mineral have the same morphology and the same crystal size.

See Table 2 below.

TABLE 2

Comparison of the HAP crystal size and morphology for the CAP/HAP bone substitute of the invention and human bone mineral

| Crystallographic axes (hexagonal space group P6$_3$/m) | CAP/HAP of the invention prepared at physiological temperature. Crystal size$^+$ [nm] | natural human bone mineral Crystal size$^+$ [nm] |
|---|---|---|
| a (1, 0, 0) | 18 (±4) | 15-21 |
| b (0, 1, 0) | 18 (±4) | 15-21 |
| c (0, 0, 1) | 38 (±8) | 34-45 |

The invention claimed is:

1. A biphasic calcium phosphate/hydroxyapatite (CAP/HAP) bone substitute material comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core, when viewed at a magnification of 3500×, has a homogeneously coarse external surface, and wherein the coarse external surface comprises flat epitactically grown nanocrystalline HAP crystal platelets.

2. The biphasic calcium phosphate/hydroxyapatite (CAP/HAP) bone substitute material according to claim 1, wherein the coarse surface comprises epitactically grown nanocrystalline hydroxyapatite platelets forming an interlocked network of platelets with sizes of 0.5 to 5 μm as determined by Scanning Electron Microscopy (SEM).

3. The biphasic calcium phosphate/hydroxyapatite (CAP/HAP) bone substitute material according to claim 1, wherein the homogeneous coarse external surface comprises epitactically grown hydroxyapatite platelets forming an interlocked network containing pores between 0.03 and 2 μm as determined by Mercury Intrusion Porosimetry (MIP).

4. The biphasic calcium phosphate/hydroxyapatite (CAP/HAP) bone substitute material according to claim 1, wherein the homogeneous coarse external surface has an Atomic Force Microscopy (AFM)-derived root mean square roughness $R_q$ in a range of 50 to 400 nm and an average maximum height of the profile $R_z$ in a range of 500 to 2000 nm.

5. The biphasic calcium phosphate/hydroxyapatite (CAP/HAP) bone substitute material according to claim 1, wherein the homogeneous coarse external surface has an Atomic Force Microscopy (AFM)-derived root mean square roughness ($R_q$) in a range of 110 to 150 nm and an average maximum height of the profile ($R_z$) in a range of 550 to 750 nm.

6. The biphasic calcium phosphate/hydroxyapatite (CAP/HAP) bone substitute material according to claim 1, wherein the sintered CAP core essentially consists of α-TCP.

7. The biphasic calcium phosphate/hydroxyapatite (CAP/HAP) bone substitute material according to claim 1, wherein the percentage of HAP is from 1.5 to 30%, as measured by X-ray diffraction (XRD).

8. The biphasic calcium phosphate/hydroxyapatite (CAP/HAP) bone substitute material according to claim 1, which is a particulate or a granulate.

9. The biphasic calcium phosphate/hydroxyapatite (CAP/HAP) bone substitute material according to claim 1, which is a shaped body.

10. A putty containing granules of a biphasic calcium phosphate/hydroxyapatite (CAP/HAP) bone substitute material according to claim 1 in a polymer matrix.

11. A process of preparing the CAP/HAP bone substitute material of claim 1, comprising the steps of
    a) preparing a sintered CAP core material,
    b) immersing the sintered CAP core material in a buffer solution containing 10 to 90% of a short-chain aliphatic alcohol at a temperature between 10° C. and 50° C. to start the transformation process of CAP to HAP to form a closed epitactically grown layer of nanocrystalline hydroxyapatite on the sintered CAP core material surface, wherein the epitactically grown nanocrystals have the same size and morphology as human bone mineral, wherein the closed epitactically grown layer of nanocrystalline HAP formed on the sintered CAP core material surface, when viewed at a magnification of 3500×, has a homogeneously coarse external surface, and wherein the coarse external surface comprises flat epitactically grown nanocrystalline HAP crystal platelets,
    c) stopping the transformation by separating solid material from the aqueous solution at a time when a closed coating of at least one nanocrystalline layer of HAP is present but before the transformation process is finished completely to form the CAP/HAP bone substitute material in which the closed epitactically grown layer of nanocrystalline HAP deposited on the external surface of the sintered CAP core, when viewed at a magnification of 3500×, has a homogeneously coarse external surface, and wherein the coarse external surface comprises flat epitactically grown nanocrystalline HAP crystal platelets, and
    d) optionally sterilizing the separated material coming from step c).

12. The process of claim 11, wherein the short-chain aliphatic alcohol is ethanol.

13. The process of claim 11, wherein the buffer solution of step b) contains 30 to 50% of a short-chain aliphatic alcohol.

14. The process of claim 11, wherein step b) is carried out at a temperature of 35 to 40° C. in a phosphate buffer solution of pH from 7.0 to 8.0 containing 20 to 60% of a short-chain aliphatic alcohol.

15. A method of promoting bone formation, bone regeneration and/or bone repair at a defect site in a subject by implanting the CAP/HAP bone substitute material of claim 1 at the defect site, such that bone formation, bone regeneration and/or bone repair are promoted at the defect site.

16. The method of claim 15, wherein the CAP/HAP bone substitute material is in the form of a granulate.

17. The method of claim 15, wherein the CAP/HAP bone substitute material is in the form of a shaped body.

18. A method of promoting bone formation, bone regeneration and/or bone repair at a defect site in a subject by implanting a putty containing granules of a biphasic calcium phosphate/hydroxyapatite (CAP/HAP) bone substitute material according to claim 1 in a polymer matrix.

19. A method of promoting osteogenic differentiation in a bone of a subject, comprising administering the CAP/HAP bone substitute material of claim 1 to the bone of a subject, such that osteogenic differentiation is promoted in the bone of the subject.

20. An implant or prosthesis, the implant or prosthesis comprising a biphasic calcium phosphate/hydroxyapatite (CAP/HAP) bone substitute material comprising a sintered CAP core and a closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core, when viewed at a magnification of 3500×, has a homogeneously coarse external surface, and wherein the coarse external surface comprises flat epitactically grown nanocrystalline HAP crystal platelets, and wherein the implant or prosthesis has a shape suitable for supporting bone formation, bone regeneration, bone repair and/or bone replacement at a defect site.

* * * * *